United States Patent
Khalaj Amineh et al.

(10) Patent No.: US 10,444,190 B2
(45) Date of Patent: Oct. 15, 2019

(54) OPTIMIZING EDDY CURRENT MEASUREMENT TO SAVE POWER

(71) Applicant: HALLIBURTON ENERGY SERVICES, INC., Houston, TX (US)

(72) Inventors: Reza Khalaj Amineh, Houston, TX (US); Burkay Dondericl, Houston, TX (US); Luis Emilio San Martin, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 202 days.

(21) Appl. No.: 15/315,339

(22) PCT Filed: Jul. 13, 2015

(86) PCT No.: PCT/US2015/040180
§ 371 (c)(1),
(2) Date: Nov. 30, 2016

(87) PCT Pub. No.: WO2016/010913
PCT Pub. Date: Jan. 21, 2016

(65) Prior Publication Data
US 2017/0131239 A1 May 11, 2017

Related U.S. Application Data

(60) Provisional application No. 62/023,865, filed on Jul. 12, 2014.

(51) Int. Cl.
*G01N 27/72* (2006.01)
*G01N 27/90* (2006.01)
*G01V 3/28* (2006.01)
*G01B 7/06* (2006.01)
(Continued)

(52) U.S. Cl.
CPC .......... *G01N 27/9006* (2013.01); *G01B 7/10* (2013.01); *G01N 27/9046* (2013.01); *G01V 3/28* (2013.01); *E21B 41/02* (2013.01); *E21B 47/0006* (2013.01)

(58) Field of Classification Search
CPC combination set(s) only.
See application file for complete search history.

(56) References Cited

U.S. PATENT DOCUMENTS 4,652,822 A 3/1987 Wallace
6,087,830 A 7/2000 Brandly et al.
(Continued)

FOREIGN PATENT DOCUMENTS

WO 2016/010913 1/2016

OTHER PUBLICATIONS

Ep Application Serial No. 15822559.9; Communication Pursuant to Rules 70(2) and 70a(2) EPC; dated Jan. 19, 2018, 1 page.
Mexican Application Serial No. MX/a/2017/000397; Mexican Official Action; dated Jun. 25, 2018, 4 pages.
Arbuzov, A. A. et al., "Memory Magnetic Imaging Defectoscopy," SPE 162054; Society of Petroleum Engineers, Russian Oil & Gas Exploration & Production Technical Conference and Exhibition held in Moscow, Russia, Oct. 16-18, 2012, 10 pgs.
(Continued)

*Primary Examiner* — Vinh P Nguyen
(74) *Attorney, Agent, or Firm* — Gilliam IP PLLC

(57) ABSTRACT

A method for optimizing eddy current measurements includes conveying an electromagnetic tool through a borehole. The method further includes transmitting an excitation signal from the tool. The method further includes recording an eddy current response to the excitation signal from one or more tubings and casings within the borehole before the fall time of the excitation signal.

14 Claims, 4 Drawing Sheets

(51) Int. Cl.
*E21B 41/02* (2006.01)
*E21B 47/00* (2012.01)

(56) References Cited

U.S. PATENT DOCUMENTS

| | | | |
|---|---|---|---|
| 6,215,304 B1* | 4/2001 | Slade | G01N 24/081 |
| | | | 324/303 |
| 6,288,548 B1* | 9/2001 | Thompson | G01V 3/30 |
| | | | 324/339 |
| 7,333,891 B2* | 2/2008 | Rabinovich | G01V 3/28 |
| | | | 702/7 |
| 7,733,084 B1 | 6/2010 | O'Dell et al. | |
| 2003/0090269 A1* | 5/2003 | Fanini | G01V 3/28 |
| | | | 324/339 |
| 2009/0195244 A1 | 8/2009 | Mouget et al. | |

OTHER PUBLICATIONS

Garcia, Javier et al., "Successful Application of a New Electromagnetic Corrosion Tool for Well Integrity Evaluation in Old Wells Completed with Reduced Diameter Tubular," IPTC 16997, Prepared for presentation at the International Petroleum Technology Conference held in Beijing, China, Mar. 26-28, 2013, 12 pgs.

PCT International Search Report and Written Opinion, dated Oct. 20, 2015, Appl No. PCT/US2015/040180, "Energy-Optimized Eddy Current Measurement Systems and Methods," filed Jul. 13, 2015, 10 pgs.

Extended European Search Report; Patent Application No. 15822559.9-1559; dated Jan. 2, 2018, 8 pages.

* cited by examiner

OPTIMIZING EDDY CURRENT MEASUREMENT TO SAVE POWER

CROSS-REFERENCE TO RELATED APPLICATIONS

This application claims priority to U.S. Provisional Application Ser. No. 62/023,865 titled "Spectrum Optimization and Dynamic Control of the Excitation in Pulsed Eddy Current Techniques," filed Jul. 12, 2014 and incorporated herein by reference.

BACKGROUND

Scaling, corrosion, precipitates, and material defects are some problems faced by the oil and gas industry when managing production well and pipeline assets. These problems lead to diminished production in wells, casing integrity failure, and pipeline integrity failure any of which may result in costly and complex remediation measures. As such, electromagnetic techniques are commonly used to monitor the condition of the production and intermediate casing strings, tubings, collars, filters, packers, and perforations. These techniques can measure magnetic field data to obtain accurate measurements of tubing thickness and tubing corrosion.

This form of corrosion monitoring can be especially useful to prevent pipe integrity failures in mature wells or non-producing wells. For example, corrosion damage typically decreases the thickness of casing strings. One electromagnetic technique used for defect detection is the pulse eddy current technique. In this technique, when a transmitter coil emits a primary electromagnetic field, or signal, eddy currents are produced in the tubings. The eddy currents produce secondary fields or signals. The transmitter coil is deactivated and/or the excitation signal is turned off and experiences a fall time. Next, a receiver coil, which has hitherto been deactivated, is activated, and the secondary signals are received by the receiver coil. When recorded and processed, the data resulting from the secondary signals can be employed to perform an evaluation of the tubings.

The eddy current technique described above is performed frequently by downhole tool as it is conveyed along a borehole. Accordingly, small inefficiencies such as minor additional power usage and slight delays in the technique become large inefficiencies such as excess power usage and significant unproductive time over the course of the run by the downhole tool and even larger inefficiencies over the lifetime of the tool.

BRIEF DESCRIPTION OF THE DRAWINGS

Accordingly, energy-optimized eddy current measurement systems and methods are disclosed herein. In the following detailed description of the various disclosed embodiments, reference will be made to the accompanying drawings in which.

Figure 1:
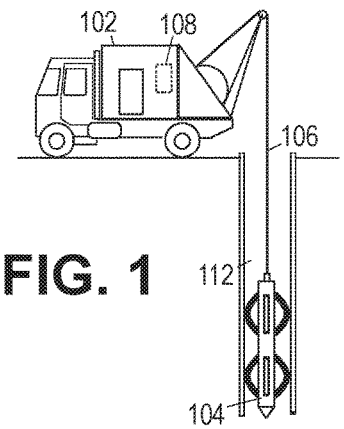
FIG. 1 is a contextual view of an illustrative wireline embodiment.

It should be understood, however, that the specific embodiments given in the drawings and detailed description thereto do not limit the disclosure. On the contrary, they provide the foundation for one of ordinary skill to discern the alternative forms, equivalents, and modifications that are encompassed together with one or more of the given embodiments in the scope of the appended claims.

NOTATION AND NOMENCLATURE

Certain terms are used throughout the following description and claims to refer to particular system components and configurations. As one of ordinary skill will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or a direct electrical or physical connection. Thus, if a first device couples to a second device, that connection may be through a direct electrical connection, through an indirect electrical connection via other devices and connections, through a direct physical connection, or through an indirect physical connection via other devices and connections in various embodiments.

DETAILED DESCRIPTION

The issues identified in the background are at least partly addressed by energy-optimized eddy current measurement systems and methods using modified excitation signals and recording responses to those excitations signals efficiently. By enabling reduced power consumption of the downhole tool for each transmission, significant power can be saved over the entire run of the downhole tool. Similarly, by reducing the time to record responses to each transmission, significant time can be saved as well. The time and power savings lead to a faster and cheaper inspection or workover operation overall.

The disclosed systems and methods for energy-optimized eddy current measurements are best understood in terms of the context in which they are employed. As such, FIG. 1 shows a contextual view of an illustrative wireline embodiment. A logging truck 102 may suspend a wireline logging tool 104 on a wireline cable 106 having conductors for transporting power to the tool 104 and telemetry from the tool 104 to the surface. The tool 104 includes one or more transmitters and receivers for performing eddy current measurements, and may further include depth sensors, temperature sensors, pressure sensors, and the like that collect other downhole measurements for tubing inspection and evaluation.

On the surface, a computer 108 acquires and stores measurement data from the tool 104 as a function of position along the borehole 112 and optionally as a function of azimuth. Though shown as an integrated part of the logging truck 102, the computer 108 may take different forms including a tablet computer, laptop computer, desktop computer, and a virtual cloud computer accessible with a thin client. The computer 108 executes software to carry out necessary processing and enables a user to view and interact with a display of the resulting information, e.g., through a graphical user interface. For example, a log of wall thicknesses or other indication of corrosion and defect locations may be displayed in pictorial or numerical form, enabling the user to initiate corrective actions if appropriate.

A processor coupled to memory may execute the software. The software may collect or obtain measurement data and organize it in a file or database. The software may also respond to user input via a keyboard or other input mechanism to display data as an image or movie on a monitor or other output mechanism such as a printer. The software may further process the data to optimize transmit signal waveforms as described below. In this way, a visual representation of the surrounding tubings may be obtained, processed, and displayed. Furthermore, the software may issue an audio or visual alert to direct the user's attention to a particular location, result, or piece of data. The processor may perform any appropriate step described below. In at least one embodiment, the tool 104 itself may include a processor coupled with memory to obtain, store, and process measurement data taken by the sensors, producing logs that are stored on a non-transient information storage medium. With respect to FIG. 1, the use of the tool 104 is shown at one position. However, the tool 104 may operate at multiple positions as the tool 104 is conveyed along the borehole.

Figure 2A:
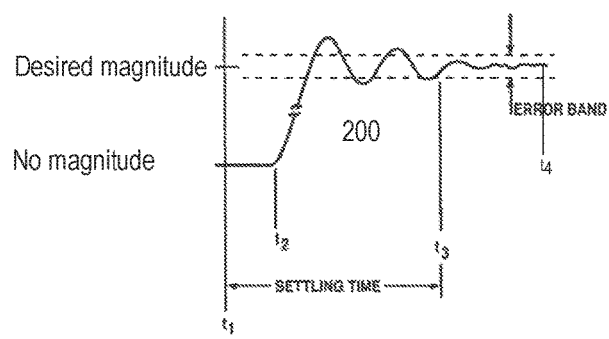
FIG. 2A is an exploded view of an illustrative rise time of an excitation signal.

FIG. 2A shows the rising edge of a rectangular excitation signal 200. Conventionally, rectangular excitation signals are used in pulse eddy current measurements. The transmitter is activated at time $t_1$, and the excitation signal begins to rise at time $t_2$. However, the signal oscillates between overshooting and undershooting the desired magnitude before settling at a steady state at the desired magnitude at time $t_4$. Similar variation is observed during the fall-time of the excitation pulse. As such, a downhole tool using rectangular excitation signals suffers from an unproductive delay each time a rectangular pulse is sent. One way to reduce the delay is to begin measuring the response at time $t_3$ while the oscillation is occurring but before a steady state has been reached. Specifically, the magnitude of the ripples in the excitation signal may be monitored. When the magnitude of the ripples lies within the error band, at $t_3$, the signal is stable enough for the purpose of measuring the response. Specifically, the error band includes a range of magnitudes. When a local peak of maximum magnitude and subsequent local valley of minimum magnitude (or alternatively a local valley and subsequent local peak as pictured) remain within the error band, then for purposes of optimizing eddy current measurements, the excitation signal has settled. This settling time occurs before the excitation signal enters a steady state. Accordingly, an amount of time equal to the difference between the settling time and the steady state time is saved each time the excitation signal is sent. Specifically, the time between $t_3$ and $t_4$ has been saved. While such time savings may be small per transmission, over the course of a single downhole run, or over the course of the lifetime of the tool, the time savings are much greater. Additionally, the pulse may be shortened thereby saving power.

Figure 2B:
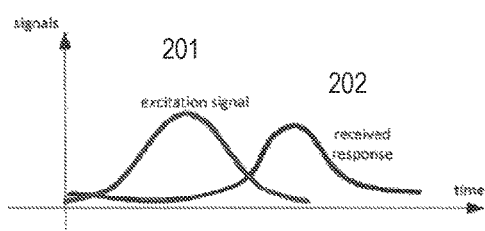
FIGS. 2B and 2C are graphs of illustrative excitation signals and received responses.
Figure 2C:
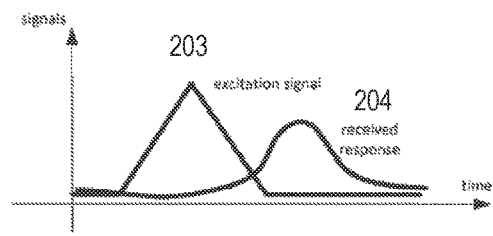

Another way to energy-optimize eddy current measurements is to shape the spectrum of the transmit signal. Specifically, a conventional rectangular excitation pulse uses many frequencies. However, not all of the frequency components may be necessary depending upon the configuration of the tubings or other downhole characteristics. FIG. 2B shows a Gaussian excitation signal 201 with a corresponding eddy current response signal 202, and FIG. 2C shows a triangular excitation signal 203 with a corresponding eddy current response signal 204. The frequency components of these unconventional excitation signals differ from the rectangular pulse. Specifically, each shaped signal includes unique spectrum of frequencies. Depending on which frequency is desired for a particular configuration of tubings, the shape may be altered by modifying the excitation signal. For example, the triangular signal incorporates harmonics at higher frequencies, which are suitable for measuring characteristics of nearby tubings in a concentric tubing configuration. If a large number of tubings are present, such as three or four concentric tubings, or the thicknesses of the tubings are large, then a Gaussian waveform concentrating energy in low frequency components is appropriate.

Figure 3:
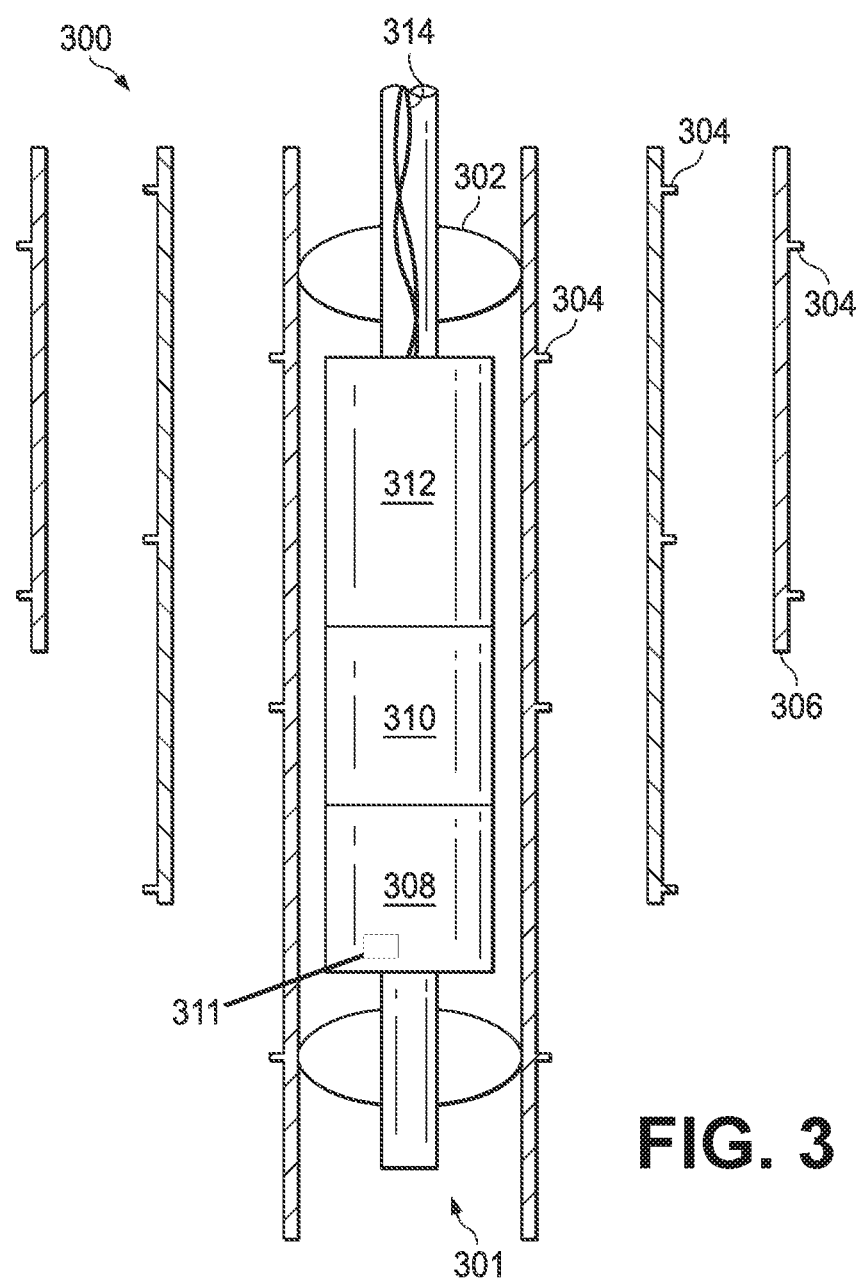
FIG. 3 is a schematic view of an illustrative downhole tool within concentric tubings.

FIG. 3 is a schematic view of an illustrative system 300 for energy-optimized eddy current measurements. The system 300 includes an electromagnetic tool 301 including an eddy current sonde module 308, a sensor module 310, a data acquisition system 312, and a control/telemetry module for communication with the surface and coordinating operation of wireline sonde instrumentation. As illustrated, the tool 301 is within three concentric tubings 306, but the tool 301 may be used with any number of tubings 306.

The sonde module 308 includes a transmitter, which may be a transmitter coil, to transmit a primary electromagnetic field that produces eddy currents in the tubings 306 and collars 304. The sonde module 308 also includes a receiver, which may be a receiver coil, to receive responses including a secondary electromagnetic field produced in response to the eddy currents. The transmitter and receiver may be operated independently, and the receiver may be activated while the transmitter is transmitting an excitation signal, e.g., before the fall of the excitation signal. The sonde module 308 also includes a pulse controller 311

The sensor module 310 includes position and orientation sensors, temperature sensors, pressure sensors, and the like that collect downhole measurements as a function of time. The data collected by these sensors may be associated with the signals transmitted and received by the sonde 308 module. For example, the received signal may be associated with downhole data corresponding to the time the signal was received. When associated, the collected measurements may provide context for interpreting and processing the signals.

The data acquisition system 312 includes a processor, memory, and communication hardware for processing operations, storing data, and enabling communications between the tool 301 and the surface. The processor may perform any appropriate steps described herein. The hardware on the tool 301 may be powered from the surface using a wireline 314 as a conduit, and the tool 301 itself may be centered within the borehole by centralizers 302. The data acquisition system may monitor the magnitude of an excitation signal with respect to an error band described with respect to FIG. 2 and may record the response based on the excitation signal settling within the error band.

The pulse controller 311 modifies the excitation signal by adjusting the timing, shape, frequency, or magnitude of the excitation signal especially in response to feedback due to monitoring of the excitation signal by the data acquisition system 312 or in response to signals received by the receiver. The pulse controller may include a digital signal processor and a digital to analog converter. The pulse controller may modify the excitation signal using a ratio of the response at multiple frequencies as described with respect to FIG. 5 below.

Figure 4:
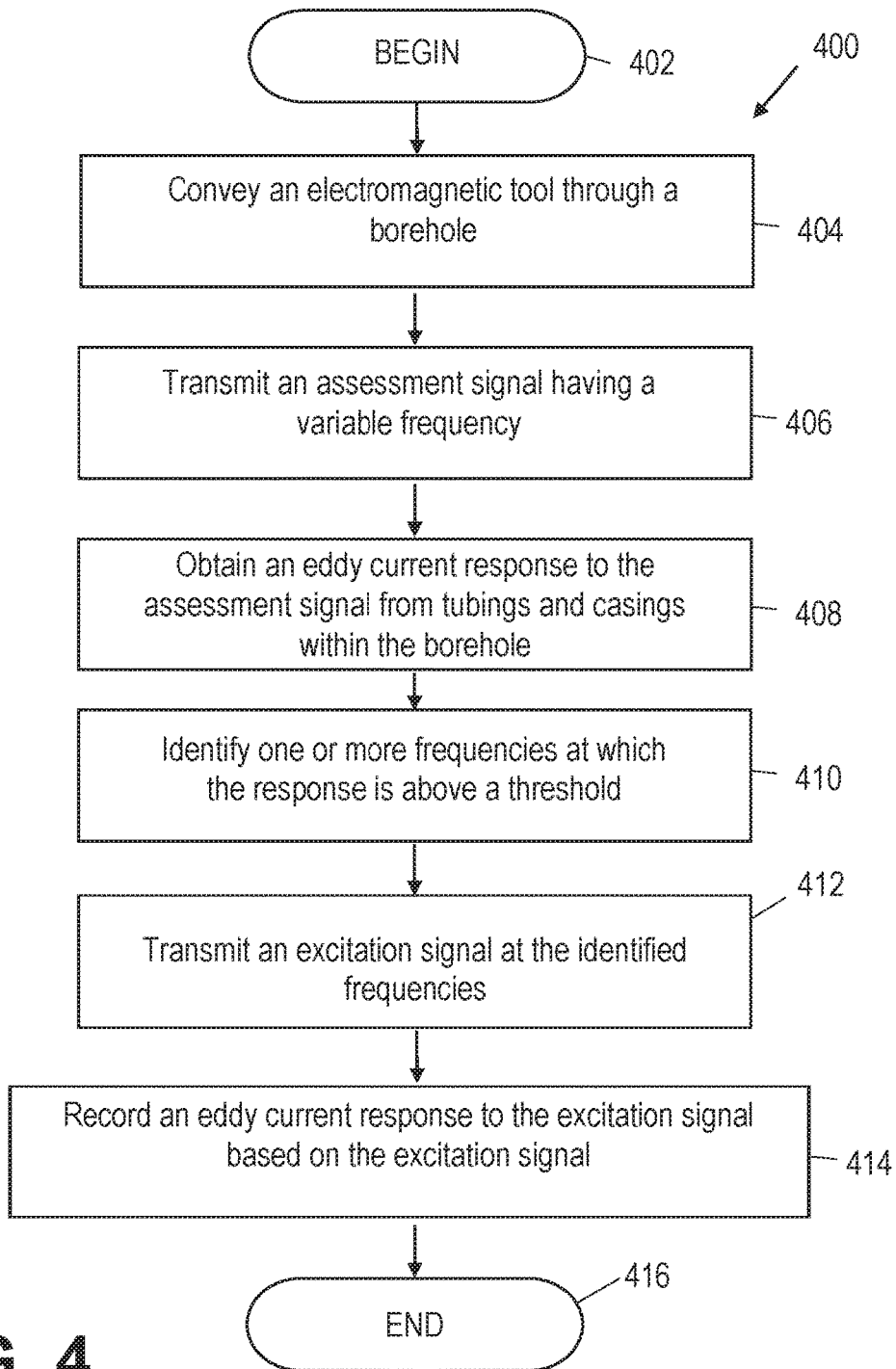
FIG. 4 is a flow diagram of a first illustrative energy-optimized eddy current measurement method.

FIG. 4 is a flow diagram of an illustrative method 400 of optimizing the energy of eddy current measurements beginning at 402 and ending at 416. At 404, an electromagnetic tool is conveyed through a borehole. The tool may be the tool illustrated in FIG. 3 and described above. The borehole includes tubings such as production tubings and a casing tubing including characteristics that may be measured using eddy current techniques such as thickness, corrosion, permeability, and the like. The tool may be conveyed through the borehole via wireline, and data processing may occur on the tool or at the surface in various embodiments.

At 406, an assessment signal including frequency that varies with time is transmitted. Sometimes called a chirp signal, the assessment signal may begin at a low frequency that linearly increases over time until a high frequency is reached. Frequencies may be between 0.1 Hz and 10 kHz. Alternatively, the assessment signal may begin at a high frequency that linearly decreases over time until a low frequency is reached.

At 408, an eddy current response to the assessment signal from one or more tubings including the casing is obtained. The transmitted signal produces eddy currents in the tubings, and the eddy currents produce a response of secondary signals. The response may be received by a receiver such as a receiving coil.

At 410, one or more frequencies at which the response to the assessment signal is above a threshold are identified. The threshold may be the average magnitude of the entire response; a fractional magnitude of the entire response; a predetermined magnitude optionally based on historical data; or a variable magnitude based on downhole characteristics such as the number of tubings, material composition of the tubings, thickness of the tubings, and the like.

At 412, an excitation signal is transmitted from the tool at the identified frequencies. By limiting the number of frequencies to only those with an above average response to the assessment signal, power is saved each time the excitation signal is sent. While such power savings may be small per transmission, over the course of a single downhole run, or over the course of the lifetime of the tool, the power savings are much greater. As the tool is conveyed along the borehole, the frequencies at which an above average response is produced may change. Accordingly, another assessment signal may be transmitted so that the new frequencies may be identified and used to generate or modify the subsequent excitation signals.

At 414, an eddy current response to the excitation signal from one or more tubings within the borehole may be recorded before the fall time of the excitation signal. For example, the response may be recorded during transmission of the excitation signal by activating a receiving coil on the tool during transmission of the excitation signal. In at least some embodiments, eddy current responses are recorded after the fall time of the excitation signal as well. If only responses after the fall time are desired, the method may further include ceasing transmission of the excitation signal after the excitation signal settles within the error band, thus saving additional power and time by not transmitting for an unnecessary length of time.

Figure 5:
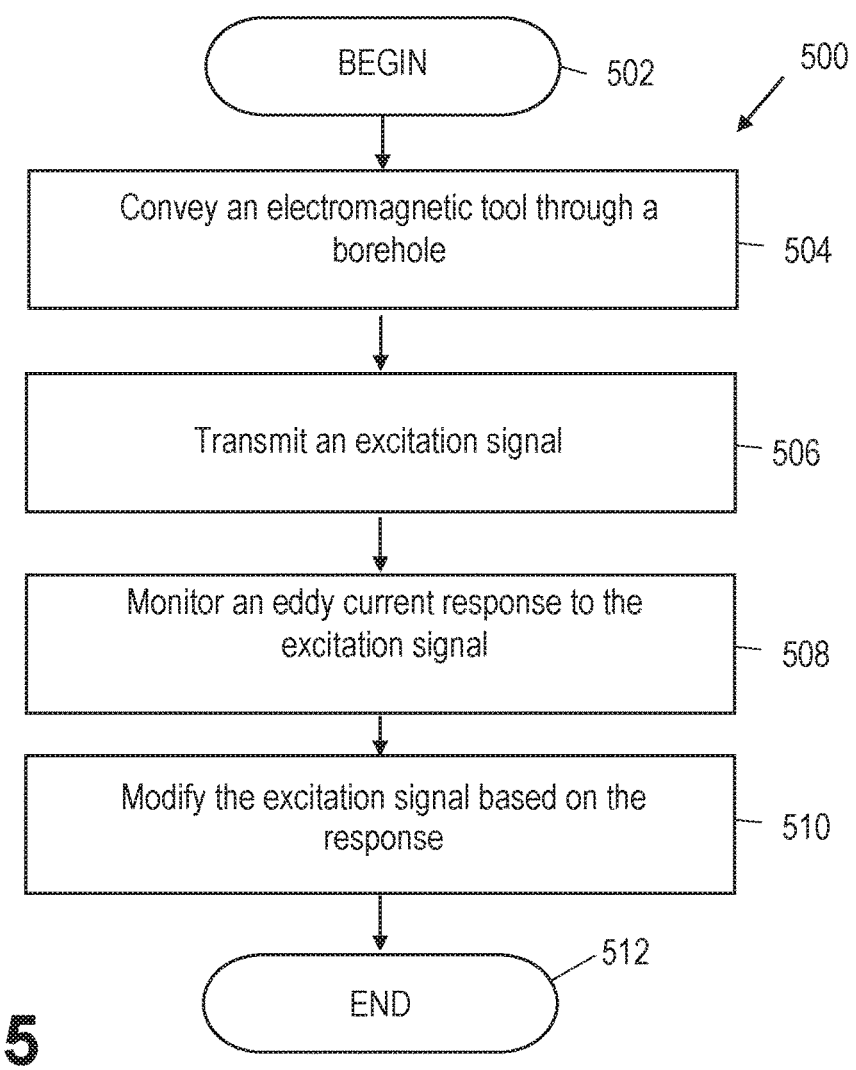
FIG. 5 is a flow diagram of a second illustrative energy-optimized eddy current measurement method.

FIG. 5 is a flow diagram of an illustrative method 500 of optimizing the energy of eddy current measurements beginning at 502 and ending at 512. At 504, an electromagnetic tool is conveyed through a borehole. The tool may be the tool illustrated in FIG. 3 and described above. The borehole includes tubings such as production tubings and a casing tubing including characteristics that may be measured using eddy current techniques such as thickness, corrosion, permeability, and the like.

At 506, an excitation signal is transmitted. For example, the excitation signal may be transmitted from a transmitter including a transmitter coil on a tool illustrated in FIG. 3. The excitation signal may include a zero direct current waveform, i.e., the excitation signal may include positive and negative portions that are equal in absolute magnitude. Such an excitation signal acts as a high pass filter that eliminates the low frequency spectrum in the eddy current technique. By eliminating the low frequency components (that are mostly useful in inspecting outer-most tubings) in the excitation signals, recording the responses for the inner-most pipes becomes power efficient.

At 508, an eddy current response to the excitation signal from one or more tubings within the borehole is monitored during transmission of the excitation signal. The response may be monitored continuously as the excitation signal is transmitted, and the excitation signal may be dynamically modified based on the monitoring at 510. Specifically, the excitation signal may be adjusted during transmission to account for above average strength at certain frequencies in the eddy current response or a quick settling of the excitation signal within the error band. For example, the excitation signal may be modified to omit certain frequencies, be shorter than conventional excitation signals, or in other power and time saving ways.

Modifying the excitation signal may include modifying the excitation signal using a ratio of the response at multiple frequencies in order to eliminate the effect of unknown signal amplitudes. For example, a ratio of signals associated with two different frequencies for the same transmitter coil and receiver may be used for a system with discrete frequency excitation. A ratio of signals associated with two different times for the same transmitter coil and receiver may be used for a system with pulsed excitation.

A method for optimizing eddy current measurements includes conveying an electromagnetic tool through a borehole. The method further includes transmitting an excitation signal from the tool. The method further includes recording an eddy current response to the excitation signal from one or more tubings and casings within the borehole before the fall time of the excitation signal.

Recording the response may include recording the response during transmission of the excitation signal. Recording the response may include activating a receiving coil on the tool during transmission of the excitation signal. The method may further include monitoring the magnitude of the excitation signal with respect to an error band including a maximum range of magnitudes between any local maximum magnitude and the next local minimum magnitude, or any local minimum magnitude and the next local maximum magnitude, and recording the response may include recording the response based on the excitation signal settling within the error band. The method may further include ceasing transmission of the excitation signal after the excitation signal settles within the error band. The method may further include recording the response after the fall time of the excitation signal. The method may further include modifying the excitation signal using a ratio of the response at multiple frequencies.

A system for optimizing eddy current measurements includes a transmitting coil to transmit an excitation signal, a receiving coil to obtain an eddy current response to the excitation signal from one or more tubings and casings within a borehole, and a data acquisition system to record the response before the fall time of the excitation signal.

The data acquisition system may monitor the magnitude of the excitation signal with respect to an error band including a maximum range of magnitudes between any local maximum magnitude and the next local minimum magnitude, or any local minimum magnitude and the next local maximum magnitude, and may record the response based on the excitation signal settling within the error band. The system may further include a pulse controller to modify the excitation signal using a ratio of the response at multiple frequencies.

A method for optimizing eddy current measurements includes conveying an electromagnetic tool through a borehole and transmitting an excitation signal from the tool. The method further includes monitoring an eddy current response to the excitation signal from one or more tubings and casings within the borehole during transmission of the excitation signal. The method further includes modifying the excitation signal based on the response.

Monitoring the response may include identifying one or more frequencies at which the response is below a threshold, and modifying the excitation signal may include eliminating the one or more frequencies from the excitation signal. The excitation signal may include a zero direct current waveform. Monitoring the response may include monitoring the magnitude of the excitation signal with respect to an error band including a maximum range of magnitudes between any local maximum magnitude and the next local minimum magnitude, or any local minimum magnitude and the next local maximum magnitude, and the method may further include recording the response based on the excitation signal settling within the error band. The method may further include ceasing transmission of the excitation signal after the excitation signal settles within the error band. The method may further include transmitting, from the tool, an assessment signal comprising frequency that varies with time, obtaining an eddy current response to the assessment signal from one or more tubings and casings within the borehole, and identifying one or more frequencies at which the response to the assessment signal is above a threshold. As such, transmitting the excitation signal may include transmitting the excitation signal including only the one or more frequencies. Modifying the excitation signal may include modifying the excitation signal using a ratio of the response at multiple frequencies.

A system for optimizing eddy current measurements includes a transmitting coil to transmit an excitation signal, a receiving coil to obtain an eddy current response to the excitation signal from one or more tubings and casings within a borehole, a data acquisition system to monitor the response during transmission of the excitation signal, and a pulse controller to modify the excitation signal based on the response.

The data acquisition system may monitor the magnitude of the excitation signal with respect to an error band including a maximum range of magnitudes between any local maximum magnitude and the next local minimum magnitude, or any local minimum magnitude and the next local maximum magnitude, and may record the response based on the excitation signal settling within the error band. The pulse controller may modify the excitation signal using a ratio of the response at multiple frequencies.

While the present disclosure has been described with respect to a limited number of embodiments, those skilled in the art will appreciate numerous modifications and variations therefrom. It is intended that the appended claims cover all such modifications and variations.

What is claimed is:

1. A method for optimizing eddy current measurements comprising:
   conveying an electromagnetic tool through a borehole;
   transmitting, from the electromagnetic tool, an excitation signal;
   monitoring a magnitude of the excitation signal with respect to an error band; and
   recording an eddy current response to the excitation signal from one or more tubings and casings within the borehole before the excitation signal falls; wherein recording the eddy current response comprises recording the eddy current response based on the excitation signal settling within the error band.

2. The method of claim 1, wherein recording the eddy current response comprises recording the eddy current response during transmission of the excitation signal.

3. The method of claim 1, wherein recording the eddy current response comprises activating a receiving coil on the electromagnetic tool during transmission of the excitation signal.

4. A method for optimizing eddy current measurements comprising:
   conveying an electromagnetic tool through a borehole;
   transmitting, from the electromagnetic tool, an excitation signal; and
   recording an eddy current response to the excitation signal from one or more tubings and casings within the borehole before the excitation signal falls; and
   monitoring a magnitude of the excitation signal with respect to an error band comprising a maximum range of magnitudes between any local maximum magnitude and the next local minimum magnitude, or any local minimum magnitude and the next local maximum magnitude, wherein recording the eddy current response comprises recording the eddy current response based on the excitation signal settling within the error band.

5. The method of claim 4, further comprising ceasing transmission of the excitation signal after the excitation signal settles within the error band.

6. The method of claim 1, further comprising recording the eddy current response after a fall time of the excitation signal.

7. The method of claim 1, further comprising modifying the excitation signal using a ratio of the eddy current response at multiple frequencies.

8. A method for optimizing eddy current measurements comprising:
   conveying an electromagnetic tool through a borehole;
   transmitting, from the electromagnetic tool, an excitation signal;
   monitoring an eddy current response to the excitation signal from one or more tubings and casings within the borehole during transmission of the excitation signal;
   recording the eddy current response; and
   modifying the excitation signal based on the eddy current response to save power during transmission of the excitation signal, wherein the modifying the excitation signal comprises omitting one or more frequencies in the excitation signal.

9. The method of claim 8, wherein monitoring the eddy current response comprises identifying one or more frequencies at which the eddy current response is below a threshold and wherein modifying the excitation signal comprises omitting the one or more frequencies at which the eddy current response is below the threshold from the excitation signal.

10. The method of claim 8, wherein the excitation signal comprises a zero direct current waveform.

11. The method of claim 8, wherein monitoring the eddy current response comprises monitoring the magnitude of the excitation signal with respect to an error band comprising a maximum range of magnitudes between any local maximum magnitude and the next local minimum magnitude, or any local minimum magnitude and the next local maximum magnitude, and further comprising recording the eddy current response based on the excitation signal settling within the error band.

12. The method of claim 11, further comprising ceasing transmission of the excitation signal after the excitation signal settles within the error band.

13. The method of claim 8, further comprising:
transmitting, from the electromagnetic tool, an assessment signal comprising frequency that varies with time;
obtaining an eddy current response to the assessment signal from one or more tubings and casings within the borehole; and
identifying one or more frequencies at which the eddy current response to the assessment signal is above a threshold;
wherein transmitting the excitation signal comprises transmitting the excitation signal comprising only the one or more frequencies at which the eddy current response to the assessment signal is above the threshold.

14. The method of claim 8, wherein modifying the excitation signal comprises modifying the excitation signal using a ratio of the eddy current response at multiple frequencies.

* * * * *

UNITED STATES PATENT AND TRADEMARK OFFICE
CERTIFICATE OF CORRECTION

PATENT NO. : 10,444,190 B2  
APPLICATION NO. : 15/315339  
DATED : October 15, 2019  
INVENTOR(S) : Reza Khalaj Amineh, Burkay Dondericl and Luis Emilio San Martin Page 1 of 1

It is certified that error appears in the above-identified patent and that said Letters Patent is hereby corrected as shown below:

On the Title Page

Item [54], insert --Optimizing Eddy Current Measurements To Save Power--

Signed and Sealed this  
Seventeenth Day of December, 2019

Andrei Iancu  
*Director of the United States Patent and Trademark Office*